United States Patent
Clarke et al.

(10) Patent No.: US 9,211,275 B2
(45) Date of Patent: Dec. 15, 2015

(54) KETONE BODIES AND KETONE BODY ESTERS AS BLOOD LIPID LOWERING AGENTS

(75) Inventors: Kieran Clarke, Oxford (GB); Richard Lewis Veech, Rockville, MD (US)

(73) Assignees: ISIS INNOVATION LTD., Oxford (GB); The United States of America, as represented by the Secretary of the Department of Health and Human Services (DHSS), Washington, DC (US)

( * ) Notice: Subject to any disclaimer, the term of this patent is extended or adjusted under 35 U.S.C. 154(b) by 162 days.

(21) Appl. No.: 12/811,648

(22) PCT Filed: Jan. 5, 2009

(86) PCT No.: PCT/US2009/030095
§ 371 (c)(1),
(2), (4) Date: Jul. 2, 2010

(87) PCT Pub. No.: WO2009/089144
PCT Pub. Date: Jul. 16, 2009

(65) Prior Publication Data
US 2010/0298294 A1    Nov. 25, 2010

Related U.S. Application Data

(60) Provisional application No. 61/018,962, filed on Jan. 4, 2008.

(51) Int. Cl.
| | | |
|---|---|---|
| *A61K 31/22* | (2006.01) |
| *A61K 31/047* | (2006.01) |
| *A61P 3/06* | (2006.01) |
| *A61K 31/19* | (2006.01) |
| *A61K 31/365* | (2006.01) |
| *A61K 45/06* | (2006.01) |

(52) U.S. Cl.
CPC .............. *A61K 31/19* (2013.01); *A61K 31/047* (2013.01); *A61K 31/22* (2013.01); *A61K 31/365* (2013.01); *A61K 45/06* (2013.01)

(58) Field of Classification Search
None
See application file for complete search history.

(56) References Cited

U.S. PATENT DOCUMENTS

| | | |
|---|---|---|
| 3,984,566 A | 10/1976 | Van Scott et al. |
| 4,380,549 A | 4/1983 | Van Scott et al. |
| 5,112,865 A | 5/1992 | Nichels et al. |
| 5,281,691 A | 1/1994 | Hubbs et al. |
| 5,654,266 A | 8/1997 | Chen et al. |
| 5,665,831 A | 9/1997 | Neuenschwander et al. |
| 5,693,850 A | 12/1997 | Birkhahn et al. |
| 6,126,953 A | 10/2000 | Costa et al. |
| 6,136,862 A | 10/2000 | Hiraide et al. |
| 6,207,856 B1 | 3/2001 | Veech |
| 6,316,038 B1 | 11/2001 | Veech |
| 6,323,237 B1 * | 11/2001 | Veech ............................ 514/450 |
| 6,380,244 B2 | 4/2002 | Martin et al. |
| 6,544,960 B1 | 4/2003 | Eldred et al. |
| 6,939,570 B1 | 9/2005 | Snow et al. |
| 7,351,736 B2 * | 4/2008 | Veech ............................ 514/450 |
| 8,101,653 B2 * | 1/2012 | Veech ............................ 514/450 |

(Continued)

FOREIGN PATENT DOCUMENTS

| | | |
|---|---|---|
| CA | 1330307 C | 6/1994 |
| CA | 2173270 A | 10/1996 |

(Continued)

OTHER PUBLICATIONS

"Glycemic Control with Diet, Sulfonylurea, Metformin, or Insulin in Patients with Type 2 Diabetes Mellitus" by Turner et al., JAMA 21, Dec. 2005 (1999).*

(Continued)

*Primary Examiner* — Theodore R West
(74) *Attorney, Agent, or Firm* — Lathrop & Gage LLP; Brian C. Trinque

(57) ABSTRACT

The subject disclosure provides compositions for reducing serum cholesterol and/or triglyceride levels in subjects. These compositions can comprise racemic β-hydroxybutyrate or D-β-hydroxybutyrate, optionally in the acid form, physiologically compatible salts of racemic β-hydroxybutyrate or D-β-hydroxybutyrate, esters of D-β-hydroxybutyrate, oligomers of D-β-hydroxybutyrate containing from 2 to 20 or more monomeric units in either linear or cyclic form, racemic 1,3 butandiol or R-1,3 butandiol alone and can be, optionally, administered in conjunction with a low fat diet to a subject. Alternatively, compositions comprising racemic β-hydroxybutyrate or D-β-hydroxybutyrate, optionally in the acid form, physiologically compatible salts of racemic β-hydroxybutyrate or D-β-hydroxybutyrate, esters of D-β-hydroxybutyrate, oligomers of D-β-hydroxybutyrate containing from 2 to 20 or more monomeric units in either linear or cyclic form, racemic 1,3 butandiol, R-1,3 butandiol or combinations thereof can be formulated as nutritional supplements (also referred to as nutritional compositions) or incorporated into therapeutic compositions containing a) anti-hypertensive agents; b) anti-inflammatory agents; c) glucose lowering agents; or d) anti-lipemic agents) which are administered to a subject, optionally in combination with a low fat diet, in order to cause a reduction or lowering of: serum cholesterol levels; triglyceride levels; serum glucose levels, serum homocysteine levels, inflammatory proteins (e.g., C reactive protein) and/or hypertension in treated subjects. Alternatively, compositions disclosed herein can be administered alone, or in combination with other therapeutic agents to prevent or reverse vascular disease.

6 Claims, No Drawings

(56) References Cited

U.S. PATENT DOCUMENTS

| | | | |
|---|---|---|---|
| 8,642,654 | B2 | 2/2014 | Clarke |
| 2001/0047008 | A1 | 11/2001 | Baraldi |
| 2002/0006959 | A1 | 1/2002 | Henderson |
| 2002/0013339 | A1 | 1/2002 | Martin et al. |
| 2002/0035231 | A1 | 3/2002 | Whitehouse et al. |
| 2003/0022937 | A1 | 1/2003 | Veech et al. |
| 2004/0063661 | A1 | 4/2004 | Linnane |
| 2004/0171671 | A1 | 9/2004 | Veech |
| 2004/0266872 | A1 | 12/2004 | Veech et al. |
| 2005/0129783 | A1 | 6/2005 | McCleary et al. |
| 2006/0280721 | A1 | 12/2006 | Veech et al. |
| 2008/0287372 | A1 | 11/2008 | Henderson |
| 2009/0197952 | A1 | 8/2009 | Hashim et al. |
| 2009/0253781 | A1 | 10/2009 | Veech |
| 2011/0237666 | A1 | 9/2011 | Clarke et al. |
| 2012/0071548 | A1 | 3/2012 | Veech |
| 2012/0213835 | A1 | 8/2012 | Neas et al. |

FOREIGN PATENT DOCUMENTS

| | | | |
|---|---|---|---|
| CN | 1483355 | A | 9/2002 |
| CN | 1552315 | A | 12/2004 |
| DE | 20205184 | U | 12/2002 |
| EP | 0552896 | A1 | 7/1993 |
| EP | 1568780 | A1 | 8/2005 |
| EP | 1809235 | B1 | 7/2007 |
| GB | 1524611 | A | 9/1978 |
| GB | 2511941 | A | 9/2014 |
| JP | S54-138126 | A | 10/1979 |
| JP | S63-112998 | A | 5/1988 |
| JP | H01-095730 | A | 4/1989 |
| JP | H01-160917 | A | 6/1989 |
| JP | H03-083950 | A | 4/1991 |
| JP | H04-112825 | A | 4/1992 |
| JP | H07-076513 | A | 3/1995 |
| JP | H10-175855 | A | 6/1998 |
| JP | H10-265378 | A | 10/1998 |
| JP | 2005247821 | | 9/2005 |
| JP | 2008127369 | A | 6/2008 |
| JP | 2009532496 | A | 9/2009 |
| JP | 2012-500264 | A | 1/2012 |
| JP | 2012500264 | A | 1/2012 |
| SU | 507322 | A | 3/1976 |
| WO | 8703806 | A1 | 7/1987 |
| WO | 9509144 | A1 | 4/1995 |
| WO | 9841200 | A1 | 9/1998 |
| WO | WO 00/04895 | | 2/2000 |
| WO | WO 00/15216 | | 3/2000 |
| WO | 0113877 | A1 | 3/2001 |
| WO | 0151645 | A1 | 7/2001 |
| WO | 2004105742 | A1 | 12/2004 |
| WO | WO 2004/108740 | | 12/2004 |
| WO | 2006020137 | A2 | 2/2006 |
| WO | 2006070337 | A2 | 7/2006 |
| WO | 2007001883 | A2 | 1/2007 |
| WO | 2007063037 | A2 | 6/2007 |
| WO | 2007115282 | A2 | 10/2007 |
| WO | 2007115934 | A1 | 10/2007 |
| WO | 2008119032 | A1 | 10/2008 |
| WO | 2008140828 | A1 | 11/2008 |
| WO | 2009023357 | A2 | 2/2009 |
| WO | 2010/021766 | A1 | 2/2010 |
| WO | 2010021766 | A1 | 2/2010 |
| WO | 2010120300 | A1 | 10/2010 |
| WO | 2011101171 | A1 | 8/2011 |
| WO | 2011121540 | A1 | 10/2011 |
| WO | 2012113415 | A1 | 8/2012 |
| WO | 2014071389 | A1 | 5/2014 |

OTHER PUBLICATIONS

"Drug Therapy of Dyslipidemia" in Goodman & Gilman's the Pharmacological Basis of Therapeutics, 11th Ed., McGraw-Hill (New York), pp. 948-953 (2006).*

International Prelminary Report on Patentablility for International Application No. PCT/US2009/030095 issued Jul. 6, 2010.

International Search Report for for International Application No. PCT/US2009/030095 issued Feb. 23, 2009.

Supplementary European Search Report and Opinion for EP 09701051.6-2123 / 2240017 PCT/US2009030095 dated Jan. 19, 2011.

Tobin, R B et al., "Effect of 1,3-Butanediol and Propionic Acid on Blood Ketones, Lipids and Metal Ions in Rats", Journal of Nutrition, vol. 102, No. 8, 1972, pp. 1001-1008.

Turner, Robert C., et al. "Glycemic control with diet, sulfonylurea, metformin, or insulin in patients with type 2 diabetes mellitus: progressive requirement for multiple therapies (UKPDS 49)." Jama 281. 21 (1999): 2005-2012.

Abdelwahab et al. (2012) "The Ketogenic Diet Is an Effective Adjuvant to Radiation Therapy for the Treatment of Malignant Glioma," Plos One. 7(5):E36197. pp. 1-7.

Boyarinov et al. (1984) "Effect of Sodium hydroxybutyrate on myocardial high-energy phosphates, function, and ultrastructure after blood loss", Biulleten' eksperimental'noĭ biologii i meditsiny. 97(3):289-292.

Buteau (2009) "Obviousness of Enantiomers over Prior Art Racemates," The Journal of High Technology Law. L22. pp. 42-49.

Clark et al. (2005) "Dilated Cardiomyopathy and Acute Liver Injury Associated with Combined Use of Ephedra, y-Hydroxybutyrate, and Anabolic Steroids" Pharmacotherapy. 25(5):756-761.

Davy et al. (1988) "Radioprotection of rat subependymal plate with 4-OH sodium butyrate," NCI Monogr. (6):231-234.

Desrochers et al. (1995) "Metabolism of {R,S)-1 ,3-butanediol acetoacetate esters, potential parenteral and enteral nutrients in conscious pigs," Am. J. Physiol. 268:E660-667.

Desrochers et al. (1995) "R, S-1, 3-butanediol acetoacetate esters, potential alternates to lipid emulsions for total parenteral nutrition," Journal of Nutritional Biochemistry. 6(2):111-118.

Desrochers et al. (1992) "Metabolism of Rand S-1 ,3-butanediol in perfused livers from meal-fed and starved rats," Biochem. J. 285:647-653.

Eagles et al. (1997) "The effects of combined treatment with β1-selective receptor antagonists and lipid-lowering drugs on fat metabolism and measures of fatigue during moderate intensity exercise: a placebo-controlled study in healthy subjects," Brit. J. Clinical Pharmacol. 43:291-300.

Edegger et al. (2006) "Regio- and Stereoselective Reduction of Diketones and Oxidation of Dials by Biocatalytic Hydrogen Transfer," Eur. J. Org. Chern. (8):1904-1909.

Felig et al. (1971) "Amino acid metabolism in exercising man," J. Clin. Invest. 50(12):2703-2714.

Goldbort et al. (1976) "Butanediols: Selection, open field activity, and NAD reduction by liver extracts in inbred mouse strains," Pharmacology Biochemistry and Behaviour. 5(3):263-268.

Kalaitzakis et al. (2005) "Highly Stereoselective Reductions of a-Aikyl-1 ,3-diketones and a-Aikyi-Jl-keto Esters Catalyzed by Isolated NADPH-Dependent Ketoreductases," Org. Lett. 7(22):4799-4801.

Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6):1530-1539.

Kohut et al. (1995) "Effects of decresased free fatty acids on fatigue during exercise with carbohydrate feedings," Medicine and Science in Sports & Exercise. 27(5 Suppl):S102.

Kulinskii et al. (1993) "The radioprotective effect of GABA-tropic substances, gamma-hydroxybutyrate and piracetam," Radiobiologiia. 33(1):133-136.—English Abstract Only.

Mori et al. (1987) "New synthesis of both enantiomers of grandisol, the boll weevil pheromon," Tetrahedron. 43 (10):2229-2239.

Nair et al. (1988) "Effect of beta-hydroxybutyrate on whole-body leucine kinetics and fractional mixed skeletal muscle protein synthesis in humans," J. Clin. Invest. 82(1):198-205.

Neubauer et al. (1997) "Myocardial Phosphocreatine-to-ATP Ratio is a predictor of mortality in patients with dilated cardiomyopathy," Circulation. 96:2190-2196.

(56) References Cited

OTHER PUBLICATIONS

Ostrovskaya et al. (1981) "Effect of prolonged administration of sodium hydroxybutyrate on the working capacity and muscle tissue in rats," Farmakologiya I Toksikologiya. 44(5):534-539.—Only English Abstract Provided.

Puchowicz et al. (2000) "Dog model of therapeutic ketosis induced by oral administration of R,S-1,3-butanediol diacetoacetate," J. Nutr. Biochem. 11:281-287.

Rossi et al. (2000) "Suppression of Feed Intake after Parenteral Administration of D—β β—Hydroxybutyrate in Pygmy Goats," J. Vet. Med. A. 47:9-16.

Shaw et al. (1984) "Influence of beta-hydroxybutyrate infusion on glucose and free fatty acid metabolism in docs," Am. J. Phys. 247:E756-764.

Sherwin et al. (1975) "Effect of ketone infusions on amino acid and nitrogen metabolism in man" J. Clin. Invest. 55(6) 1382-1390.

Simons et al. (1982) "Long term treatment with Slow Release Oxprenolol Alone, or in Combination with other Drugs: Effects on Blood Pressure, Lipoproteins and Exercise Performance," Aust. N. Z. J. Med. 12:612-616.

Smith et al. (1975) "Initial effect of injury on ketone bodies and other blood metabolites," Lancet. 1(7897):1-3.

Wu et al. (1987) "Ketone bodies inhibit leucine degradationin chick skeletal muscle," International J. Of Biochem. 19 (10):937-943.

Zhu et al. (2006) "A recombinant ketoreductase tool-box. Assessing the substrate selectivity and stereoselectivity toward the reduction of Jl-ketoesters," Tetrahedron. 62:901-905.

International Search Report with Written Opinion corresponding to International Patent Application No. PCT/EP2014/067027, mailed Oct. 30, 2014.

International Search Report corresponding to International Patent Application No. PCT/EP2014/055158, mailed Jun. 25, 2014.

International Search Report with Written Opinion corresponding to International Patent Application No. PCT/US2013/068545, mailed Jan. 20, 2014.

International Search Report with Written Opinion corresponding to International Patent Application No. PCT/EP2013/057250, mailed Jun. 11, 2013.

International Search Report and Written Opinion corresponding to International Patent Application No. PCT/EP2011/000833, mailed Jun. 22, 2011.

International Search Report corresponding to International Patent Application No. PCT/EP2013/069189, mailed Aug. 12, 2014.

International Preliminary Report on Patentability corresponding to International Patent Application No. PCT/US2009/040773, issued Oct. 18, 2011.

International Search Report with Written Opinion corresponding to International Patent Application No. PCT/US2004/018016, mailed Apr. 15, 2005.

International Search Report with Written Opinion corresponding to International Patent Application No. PCT/GB2004/002286, mailed Oct. 11, 2004.

Search and Examination Report corresponding to Great Britain Patent Application No. 1414016.4, dated Aug. 29, 2014.

Search Report corresponding to Great Britain Patent Application No. 1304467.2, dated Aug. 23, 2013.

Search Report corresponding to Great Britain Patent Application No. 1002983.3, dated Jun. 10, 2010.

Search and Examination Report corresponding to Great Britain Patent Application No. 1404400.2, dated Mar. 26, 2014.

Supplementary European Search Report and Written Opinion corresponding to European Patent Application No. 09701051.6, dated Jan. 19, 2011.

Search and Examination Report corresponding to Great Britain Patent Application No. 1404577.7, dated Oct. 23, 2014.

Search Report corresponding to Great Britain Patent Application No. 1314127.0, dated Jan. 31, 2014.

International Search Report with Written Opinion corresponding to Interntational Patent Application No. PCT/US2009/040766, mailed Aug. 6, 2009.

International Search Report with Written Opinion corresponding to Interntational Patent Application No. PCT/US2009/040773, mailed Feb. 22, 2010.

Larios et al. (2004) "Synthesis of flavor and fragrance esters using Candida antarctica lipase," Appl. Microbiol. Biotechnol. 65:373-376.

\* cited by examiner

KETONE BODIES AND KETONE BODY ESTERS AS BLOOD LIPID LOWERING AGENTS

CROSS-REFERENCE TO RELATED APPLICATIONS

This is a U.S. national stage application of International Application No. PCT/US2009/030095 filed on Jan. 5, 2009 which claims the benefit of and priority to U.S. Provisional Application Ser. No. 61/018,962, filed Jan. 4, 2008, both of which are hereby incorporated herein by reference in its their entirety, including all figures, tables and amino acid or nucleic acid sequences.

This invention was made with government support under Grant No. W911 NF-05-1-0479 awarded by ARMY/ARO. The U.S. Government has certain rights in the invention.

BACKGROUND OF THE INVENTION

Vascular insufficiency, secondary to occlusive processes in the vasculature, constitutes a disease phenotype of wide applicability in a number of common disease states including among others: coronary insufficiency, cerebrovascular insufficiency, peripheral vascular insufficiency and impaired kidney perfusion. Among the major known pre-disposing factors causing narrowing of vasculature are: 1) elevated serum cholesterol, 2) elevated serum triglycerides, 3) elevated serum glucose, 4) elevated serum homocysteine, 5) certain inflammatory processes and 6) hypertension.

Ketone bodies cannot be utilized by liver, hence they can not be used to synthesize either triglycerides or cholesterol. Triglycerides and cholesterol are synthesized either from carbohydrates or lipids, which provide acetyl CoA, and thence respectively malonyl CoA or HMG CoA for the two synthetic pathways. The major source of blood cholesterol and triglyceride comes from liver where it is excreted into the blood as VLDL, the fatty acids of which are removed by various tissues to leave LDL in the blood.

The inventors of the subject patent application have found that feeding a subject a diet comprising, in part, esters or oligomers of the ketone body D-β-hydroxybutyrate and lowered dietary fat can reverse a number of the known predisposing factors leading to vascular diseases.

BRIEF SUMMARY OF THE INVENTION

The subject disclosure provides compositions for reducing serum cholesterol and/or triglyceride levels in subjects. These compositions can comprise racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol or any combination thereof alone and can be, optionally, administered in conjunction with a low fat diet to a subject. Alternatively, compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol or any combination thereof can be formulated as nutritional supplements (also referred to as nutritional compositions) or incorporated into therapeutic compositions (compositions combining racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol or any combination thereof and a) anti-hypertensive agents; b) anti-inflammatory agents; c) glucose lowering agents; or d) anti-lipemic agents) which are administered to a subject, optionally in combination with a low fat diet, in order to cause a reduction or lowering of: serum cholesterol levels; triglyceride levels; serum glucose levels, serum homocysteine levels, inflammatory proteins (e.g., C reactive protein) and/or hypertension in treated subjects. Alternatively, racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol or any combination thereof can be administered alone, or in combination with other therapeutic agents to prevent or reverse vascular disease.

BRIEF DESCRIPTION OF THE TABLES

Table 1 provides details related to the diets fed to experimental animals.

Table 2 relates to plasma metabolite levels in non-fasting rats fed one of three diets for 7 or 66 days. The ketone diet doubled the plasma β-hydroxybutyrate concentrations at both 7 and 66 days. Total cholesterol levels were significantly lower in ketone-fed rats compared with rats fed a Western diet. After 66 days on the diets, plasma HDL and LDL levels were significantly lower, and the HDL/LDL ratios tended to be higher, in the ketone fed rats compared with the Western-diet fed rats. The triacylglycerol levels were significantly lower in the rats fed the ketone diet, compared with rats fed the Western diet. There were no effects of diet on plasma free fatty acid levels, but the rats fed the ketone diet for 66 days had lower plasma glucose levels.

Table 3 provides a listing of combination therapies used for the treatment of hypertension.

DETAILED DESCRIPTION OF THE INVENTION

The subject disclosure provides compositions for reducing serum cholesterol and/or triglyceride levels in subjects. These compositions can comprise racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof alone. Alternatively, compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof can be formulated as nutritional supplements (also referred to as nutritional compositions) or incorporated into therapeutic compositions (compositions combining racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof and a) anti-hypertensive agents; b) anti-inflammatory agents; c) glucose lowering agents; or d) anti-lipemic agents) which are administered to a subject in order to cause a reduction or lowering of: serum cholesterol levels; triglyceride levels; serum glucose levels, serum homocysteine levels, inflammatory proteins (e.g., C reactive protein) and/or hypertension in treated subjects. Alternatively, racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof can be administered alone in a normal diet, or in combination with other therapeutic agents to prevent or reverse vascular disease. In any of these embodiments, the compositions can be administered to a subject in combination with a low fat diet.

The subject application provides compositions comprising racemic β-hydroxybutyrate or D-β-hydroxybutyrate (optionally in the acid form), physiologically compatible salts of racemic 3-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof in combination with:
a) anti-lipemic agents;
b) anti-hypertensive agents (including those combination treatments set forth in the table entitled "Combination Drugs for Treatment of Hypertension" [Table 3]);
c) glucose lowering agents; or
d) anti-inflammatory agents.

Non-limiting examples of anti-hypertensive agents that can be used in the formulation of compositions according to the subject invention include, and are not limited to, captopril (CAPOTEN), benazepril (LOTENSIN), enalapril (VASOTEC), lisinopril (PRINIVIL, ZESTRIL) fosinopril (MONOPRIL), ramipril (ALTACE), perindopril (ACEON), quinapril (ACCUPRIL), moexipril (UNIVASC), trandolapril (MAVIK), candesartan (ATACAND), eprosartan (TEVETAN), irbesartan (AVAPRO), telmisartan (MYCARDIS), valsartan (DIOVAN), losartan (COZAAR), atenolol (TENORMIN), propranolol (INDERAL), metoprolol (TOPROL), nadolol (CORGARD), betaxolol (KERLONE), acebutolol (SECTRAL), pindolol (VISKEN), bisoprolol (ZEBETA), hydrochlorothiazide (HYDRODIURIL), furosemide (LASIX), torsemide (DEMADEX), the combination of triamterene and hydrochlorothiazide (DYAZIDE), metolazone (ZAROXOLYN), ethacrynic acid, nisoldipine (SULAR), nifedipine (ADALAT, PROCARDIA), nicardipine (CARDENE), bepridil (VASCOR), isradipine (DYNACIRC), nimodipine (NIMOTOP), felodipine (PLENDIL), amlodipine (NORVASC), diltiazem (CARDIZEM), verapamil (CALAN, ISOPTIN), terazosin (HYTRIN), doxazosin (CARDURA), tamsulosin (FLOMAX), alfuzosin (UROXATRAL) or clonidine (CATAPRES) and the combination therapies disclosed in the table below (entitled "Combination Drugs for Treatment of Hypertension" (Table 3)). These agents are formulated with racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof to provide compositions useful for the reduction or lowering hypertension in treated subjects. These compositions can also be used to prevent or reverse vascular disease in a subject.

With respect to glucose lowering agents, there are four major classes of oral glucose lowering agents. These include the biguanides (e.g., metformin), sulfonylureas (e.g., glyburide), thiazolidinediones and alpha-glucosidase inhibitors. Thus, the subject invention also provides compositions comprising D-β-hydroxybutyrate and esters or precursors thereof in combination with biguanides (e.g., metformin), sulfonylureas (e.g., glyburide), thiazolidinediones and/or alpha-glucosidase inhibitors that are useful for lowering blood glucose levels in a subject.

The subject invention also provides compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof in combination with anti-lipemic agents (e.g., probucol, niacin, omega 3 ethyl esters or omega 3 fatty acids), bile acid sequesterants (e.g., cholestyramine, cholestyramine-sucrose, cholestyramine-aspartame, colesevelam or colestipol), cholesterol absorption inhibitors (e.g., ezetimibe or ezetimibe-simvastatin) fibric acid derivatives (e.g., fenofibrates or gemfibrozil), and/or HMG-CoA reductase inhibitors (amlodipine-atorvastatin, atorvastatin, fluvastatin, lovastatin, niacin-lovastatin, pravastatin, rosuvastatin, simvastatin). Such compositions can be used to reduce or lower serum cholesterol levels or triglyceride levels in a subject.

Compositions comprising anti-inflammatory agents and racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof are also provided by the subject application. Anti-inflammatory agents include, but are not limited to: aspirin, salsalate, diflunisal, ibuprofen, ketoprofen, nabumetone, piroxicam, naproxen, diclofenac, indomethacin, sulindac, tolmetin, etodolac, ketorolac, oxaprozin or celecoxib. Thus, the subject invention also provides for the treatment of inflammation comprising the administration of compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof alone, or in combination with anti-inflammatory agents.

The subject invention also provides for the use of the aforementioned compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof for the preparation of a medicament for lowering or reducing serum cholesterol; triglyceride levels; serum glucose levels, serum homocysteine levels, inflammatory proteins (e.g., C reactive protein) and/or hypertension in a subject. The use described in this paragraph can optionally comprise the administration of the aforementioned compositions to a subject in conjunction with the administration of a low fat diet to a subject.

Thus, in one embodiment of the invention, a use of a composition, as described above, comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof (alone or in combination with other agents (e.g., a) anti-lipemic agents; b) anti-hypertensive agents (including those combination treatments set forth in Table 3, entitled "Combination Drugs for Treatment of Hypertension"); c) glucose lowering agents; or d) anti-inflammatory agents)) to lower or reduce serum cholesterol levels; triglyceride levels; serum glucose levels, serum homocysteine levels, inflammatory proteins (e.g., C reactive protein) and/or hypertension in a subject is provided. These compositions can be administered to a subject orally (e.g., in the form of the diet of the subject (a nutritional composition for example) or via the administration of therapeutic compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof), parenterally, via injection or rectally. Again, the compositions described herein can be administered alone or in conjunction with a low fat diet to the subject.

In certain preferred embodiments, the methods of the subject application comprise the oral administration of compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof. These orally administered compositions have the benefit of lowering serum cholesterol, triglyceride and/or glucose levels in a subject, including those instances where the compositions are orally administered as a part of a low fat diet to the subject. For the purposes of this invention, the term "subject" is directed to mammals and, in certain embodiments, humans. "Administering" "administered" or "administer" is defined as the introduction of the disclosed compositions into a subject via oral, nasal, ocular, rectal, vaginal and parenteral routes.

Compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof may be administered alone (e.g., a composition comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof and lacking any other therapeutic ingredient) or in combination with other agents (e.g., a) anti-lipemic agents; b) anti-hypertensive agents (including those combination treatments set forth in Table 3, entitled "Combination Drugs for Treatment of Hypertension"); c) glucose lowering agents; or d) anti-inflammatory agents) via any route of administration and, optionally, in conjunction with the administration or intake of a low fat diet by the subject. These routes of administration include, and are not limited to, subcutaneous (SQ), intramuscular (IM), intravenous (IV), intraperitoneal (IP), intradermal (ID), via the nasal, ocular or oral mucosa (IN), or orally (PO). When the compositions disclosed herein are administered orally, the compositions can be provided to the subject in the form of the diet eaten by the subject or in pills or other unit dose forms. A unit dose form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge. As described herein, the phrase "in combination" is to be interpreted as the administration of compositions comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof with other agents either together (in a single composition), separately (i.e., a first composition comprising racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof and a second composition comprising another agent (e.g., a) anti-lipemic agents; b) anti-hypertensive agents (including those combination treatments set forth in the table entitled "Combination Drugs for Treatment of Hypertension" [Table 3]); c) glucose lowering agents; or d) anti-inflammatory agents)) or sequentially. For the sequential administration of a first and second composition to be considered a combination therapy (e.g., "in combination"), the first and second compositions must be administered separated by a time interval that still permits the first composition to be used during a treatment cycle of the second composition, or that permits the first composition to show enhanced activity, particularly activity, when compared with the single components alone. In the context of this invention, the term "activity" relates to an ability to lower serum cholesterol levels; triglyceride levels; serum glucose levels, blood sugar levels, serum homocysteine levels, inflammatory proteins, inflammation or blood pressure/hypertension.

Racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof are administered to an individual in an amount that results in blood concentrations of between 0.1 to 25 mM of D-β-hydroxybutyrate plus acetoacetate, or preferably between 0.4 to 10 mM or most preferred between 0.6 and 3 mM blood levels of D-β-hydroxybutyrate plus acetoacetate. Alternatively, the methods may recite the levels of racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof that are to be administered to an individual in terms of percentages. Thus, racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol, R-1,3 butandiol, or any combination thereof can be administered in amounts that range from 2-100% of the diet of an individual, or preferably 5-70% of the diet of an individual, or most preferred 5-30% of the diet of the individual. These percentages refer to the total caloric intake of the individual. Additionally, any combination of racemic β-hydroxybutyrate or D-β-hydroxybutyrate (optionally in the acid form), physiologically compatible salts of racemic β-hydroxybutyrate or D-β-hydroxybutyrate (e.g., sodium, potassium, calcium or magnesium salts), esters of D-β-hydroxybutyrate, oligomers of D-β-hydroxybutyrate containing from 2 to 20 (or more) monomeric units in either linear or cyclic form, racemic 1,3 butandiol or R-1,3 butandiol can be administered to an individual in accordance with the aforementioned methods.

EXAMPLES

Animals were fed diets comprising the various components as set forth in Table 1. The animals were then tested to determine total cholesterol levels, low density lipoprotein levels, high density lipoprotein levels, triacylglycerol levels, free fatty acid levels and plasma glucose levels. Table 2 relates to plasma metabolite levels in non-fasting rats fed one of three diets for 7 or 66 days. The ketone diet doubled the plasma β-hydroxybutyrate concentrations at both 7 and 66 days. Total cholesterol levels were significantly lower in ketone-fed rats compared with rats fed a Western diet. After 66 days on the diets, plasma HDL and LDL levels were significantly lower, and the HDL/LDL ratios tended to be higher, in the ketone fed rats compared with the Western-diet fed rats. The triacylglycerol levels were significantly lower in the rats fed the ketone diet, compared with rats fed the Western diet. There were no effects of diet on plasma free fatty acid levels, but the rats fed the ketone diet for 66 days had lower plasma glucose levels.

TABLE 1

Diet macronutrient composition. All diets contained the same energy (kcal/g), but had different macronutrients.

| Diet | Energy (kcal/g) | Fat | Protein | Carbohydrate (% kcal) | Ketone |
|---|---|---|---|---|---|
| Western | 1.76 | 34 | 27 | 39 | 0 |
| Carbohydrate | 1.76 | 4 | 26 | 70 | 0 |
| Ketone | 1.76 | 4 | 27 | 39 | 30 |

TABLE 2

Non-fasting rat plasma metabolite levels measured after feeding a Western, high carbohydrate or ketone diet for 7 (upper section) or 66 ± 3 days (lower section).

| Plasma metabolites after 7 days on diet | Western diet (n = 10) | Ketone diet (n = 10) |
|---|---|---|
| β-Hydroxybutyrate (mM) | 0.41 ± 0.03 | 0.85 ± 0.10*** |
| Cholesterol (mM) | 1.9 ± 0.1 | 1.2 ± 0.1*** |
| Triacylglycerol (mM) | 1.95 ± 0.15 | 0.79 ± 0.11** |
| Free fatty acids (mM) | 0.11 ± 0.01 | 0.15 ± 0.02 |
| Glucose (mM) | 15 ± 1 | 14 ± 1 |

| Plasma metabolites after 66 days on diet | Western diet (n = 10) | Carbohydrate diet (n = 10) | Ketone diet (n = 10) |
|---|---|---|---|
| β-Hydroxybutyrate (mM) | 0.48 ± 0.06 | 0.59 ± 0.14 | 0.91 ± 0.20* |
| Cholesterol (mM) | 2.3 ± 0.2 | 1.6 ± 0.2 | 1.1 ± 0.1*** |
| HDL (mM) | 0.69 ± 0.03 | 0.47 ± 0.04*** | 0.33 ± 0.05*** |
| LDL (mM) | 0.22 ± 0.03 | 0.13 ± 0.03* | 0.09 ± 0.02*** |
| HDL/LDL | 3.4 ± 0.3 | 4.2 ± 0.6 | 4.4 ± 0.5 |
| Triacylglycerol V | 1.11 ± 0.13 | 0.92 ± 0.09 | 0.67 ± 0.11*** |
| Free fatty acids (mM) | 0.23 ± 0.09 | 0.23 ± 0.03 | 0.26 ± 0.04 |
| Glucose (mM) | 12.8 ± 0.42 | 14.9 ± 2.1 | 8.6 ± 1.1** |

*$P < 0.05$;
**$P < 0.01$;
***$P < 0.001$ vs. Western diet.

TABLE 3

Combination Drugs for Treatment of Hypertension amiloride and hydrochlorothiazide
spironolactone and hydrochlorothiazide
triamterene and hydrochlorothiazide
triamterene and hydrochlorothiazide
atenolol and chlorthalidone
bisoprolol and hydrochlorothiazide
metoprolol and hydrochlorothiazide
nadolol and bendroflumethazide
propranolol and hydrochlorothiazide
propranolol and hydrochlorothiazide
timolol and hydrochlorothiazide
benazepril and hydrochlorothiazide
captopril and hydrochlorothiazide
enalapril and hydrochlorothiazide
lisinopril and hydrochlorothiazide
lisinopril and hydrochlorothiazide
moexipril and hydrochlorothiazide
losartan and hydrochlorothiazide
valsartan and hydrochlorothiazide
amlodipine and benazepril TABLE 3-continued Combination Drugs for Treatment of Hypertension diltiazem and enalapril
felodipine and enalapril
verapamil and trandolapril
clonidine and chlorthalidone
hydralazine and hydrochlorothiazide
methyldopa and hydrochlorothiazide
prazosin and polythiazide

We claim:

1. A method for lowering at least one of serum cholesterol level, triglyceride level and serum glucose level in a healthy non-diabetic subject in need thereof, comprising administering to the subject a composition comprising a R-1,3 butandiol ester of D-β-hydroxybutyrate alone, or in combination with an additional therapeutic agent, to a subject so as to raise blood D-β-hydroxybutyrate plus acetoacetate from between 0.1 to 20 mM.

2. The method according to claim 1, wherein said composition comprising a R-1,3 butandiol ester of D-β-hydroxybutyrate alone is administered in the form of the subject's diet.

3. The method according to claim 1, wherein said method comprises administering to the subject a first composition comprising a R-1,3 butandiol ester of D-β-hydroxybutyrate in combination with a second composition comprising a therapeutic agent, wherein said first and second compositions are administered separately, sequentially or together and each composition is in unit a dosage form.

4. The method according to claim 3, wherein said therapeutic agent is selected from the group consisting of captopril, benazepril, enalapril, lisinopril fosinopril, ramipril, perindopril, quinapril, moexipril, trandolapril, candesartan, eprosartan, irbesartan, telmisartan, valsartan, losartan, atenolol, propranolol, metoprolol, nadolol, betaxolol, acebutolol, pindolol, bisoprolol, hydrochlorothiazide, furosemide, torsemide, the combination of triamterene and hydrochlorothiazide, metolazone, ethacrynic acid, nisoldipine, nifedipine, nicardipine, bepridil, isradipine, nimodipine, felodipine, amlodipine, diltiazem, verapamil, terazosin, doxazosin, tamsulosin, alfuzosin, clonidine, biguanides, sulfonylureas, thiazolidinediones, alpha-glucosidase inhibitors, probucol, niacin, omega 3 ethyl esters, omega 3 fatty acids, bile acid sequesterants, cholestyramine, cholestyramine-sucrose, cholestyramine-aspartame, colesevelam, colestipol, cholesterol absorption inhibitors, ezetimibe, ezetimibe-simvastatin, fibric acid derivatives, fenofibrates, gemfibrozil, HMG-CoA reductase inhibitors, amlodipine-atorvastatin, atorvastatin, fluvastatin, lovastatin, niacin-lovastatin, pravastatin, rosuvastatin, simvastatin, aspirin, salsalate, diflunisal, ibuprofen, ketoprofen, nabumetone, piroxicam, naproxen, diclofenac, indomethacin, sulindac, tolmetin, etodolac, ketorolac, oxaprozin and celecoxib.

5. The method according to claim 1, wherein the dietary intake of fat by said subject is reduced or the subject is consuming a low fat diet.

6. The method according to claim 1, wherein the R-1,3 butanediol ester of D-β-hydroxybutyrate is administered in an amount that a) provides for blood levels of D-β-hydroxybutyrate plus acetoacetate ranging from between 0.1 to 25 mM; or b) ranging from 2-100% of the total caloric intake of the subject.

* * * * *